US012611503B2

(12) United States Patent
Ryan

(10) Patent No.: US 12,611,503 B2
(45) Date of Patent: Apr. 28, 2026

(54) SYSTEM AND METHOD FOR SEQUENTIAL DELIVERY OF THERAPEUTIC COMPOSITIONS

(71) Applicant: Becton, Dickinson and Company, Franklin Lakes, NJ (US)

(72) Inventor: Kevin M. Ryan, Whitehouse Station, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 670 days.

(21) Appl. No.: 17/968,258

(22) Filed: Oct. 18, 2022

(65) Prior Publication Data

US 2024/0123137 A1      Apr. 18, 2024

(51) Int. Cl.
A61M 5/14 (2006.01)
A61M 5/168 (2006.01)

(52) U.S. Cl.
CPC ...... A61M 5/1417 (2013.01); A61M 5/16881 (2013.01); A61M 5/1689 (2013.01)

(58) Field of Classification Search
CPC .............. A61M 5/1417; A61M 5/1411; A61M 5/16881; A61M 5/1689; A61M 5/16827; A61M 2005/6009; A61M 2005/3334; A61M 2005/1787; A61M 5/172; A61M 5/168; A61M 5/16877; G16H 20/17

USPC .......................................................... 604/500
See application file for complete search history.

(56) References Cited

U.S. PATENT DOCUMENTS

| | | | | |
|---|---|---|---|---|
| 4,705,506 A | * | 11/1987 | Archibald ......... | A61M 5/16827 |
| | | | | D24/129 |
| 6,017,318 A | * | 1/2000 | Gauthier .............. | A61M 39/16 |
| | | | | 604/258 |
| 2012/0283630 A1 | * | 11/2012 | Lee ........................ | G16H 20/17 |
| | | | | 604/65 |
| 2016/0123355 A1 | * | 5/2016 | Collins .............. | F15B 13/0444 |
| | | | | 137/596.14 |
| 2017/0021091 A1 | * | 1/2017 | Alkire ................. | A61M 5/1415 |
| 2020/0188586 A1 | * | 6/2020 | Sims ................. | A61M 5/16877 |

* cited by examiner

*Primary Examiner* — Mark A Laurenzi
*Assistant Examiner* — Kelsey L Stanek
(74) *Attorney, Agent, or Firm* — Servilla Whitney LLC

(57) ABSTRACT

Provided herein is a system for sequential delivery of therapeutic compositions, including a first fluid source and a second fluid source, one or more first sensors associated with each of the first fluid source and the second fluid source, an actuator-actuated valve, and a processor in communication with the one or more sensors, wherein the processor is programmed or configured to control, based on data received from the one or more sensors, the actuator-actuated valve to stop and/or cause delivery of therapeutic compositions from the fluid sources.

31 Claims, 9 Drawing Sheets

SYSTEM AND METHOD FOR SEQUENTIAL DELIVERY OF THERAPEUTIC COMPOSITIONS

BACKGROUND OF THE INVENTION

Field of the Invention

The present disclosure relates generally to systems for use with intravenous fluid delivery, and, more specifically, to systems for sequential delivery of therapeutic compositions.

Description of Related Art

In the practice of intravenous (IV) Infusion "Piggy-Backing", the clinician will often have to spend time adjusting the relative heights of each medication bag in order to achieve the proper flow rate and the proper flow sequence. Typically, this is accomplished by placing/adjusting the IV medication bag height such that it is higher than the saline bag, such that the increased head pressure of the medication bag will bias the flow from that bag, before the flow of the saline bag. There are typically check valves and roller/variable pinch valves in place as to further help bias the flow dynamics of the system.

However, performing these adjustments manually is difficult and time-consuming. In addition, once the system starts flowing, the head pressure continuously changes corresponding with the draining of the IV bags, which lowers the head pressure. This is compounded by any pressure changes in the patient or flow obstructions in the IV line. All these factors affect the medication flow rate away from the nominal medication prescription parameters ordered by the physician. If the flow biasing is not done correctly or if the changes that occur in the lines during the infusion are great enough, the flow sequencing may reverse, in that the saline will flow before the medication (e.g., out of sequence). In this case, the medical outcome could be severe, especially in cases of oncology. Accordingly, there is a need in the art for systems that can provide highly accurate delivery of therapeutic compositions.

SUMMARY OF THE INVENTION

Provided herein is a system for sequential delivery of therapeutic compositions, including a first fluid source and a second fluid source, one or more first sensors associated with each of the first fluid source and the second fluid source, an actuator-actuated valve including a valve manifold having a first inlet port, a second inlet port, and an outlet port, wherein the first inlet port is in fluid communication with the first fluid source and the second inlet port is in fluid communication with the second fluid source, a valve spool extending within the valve manifold, the valve manifold and valve spool defining a first valve passageway and a second valve passageway, wherein the valve spool is moveable relative to the valve manifold between a first position in which the first inlet port and the outlet port are in fluid communication via the first valve passageway and a second position in which the second inlet port and the outlet port are in fluid communication via the second valve passageway, an actuator configured to displace the valve spool relative to the valve manifold between the first position and the second position, and a processor in communication with the one or more sensors, wherein the processor is programmed or configured to control, based on data received from the one or more sensors, the actuator to displace the valve spool relative to the valve manifold between the first position and the second position.

In certain configurations, the first fluid source and/or the second fluid source are intravenous (IV) drip bags.

In certain configurations, the one or more first sensors include a first flow sensor associated with the first fluid source and a second flow sensor associated with the second fluid source.

In certain configurations, the flow sensors are drip counters.

In certain configurations, the IV drip bags are suspended and the flow sensors are arranged beneath the IV drip bags.

In certain configurations, the processor is further programmed or configured to control the actuator to move from the first position to the second position when a pre-determined volume of fluid has been dispensed from the first fluid source.

In certain configurations, the processor is further programmed or configured to control the actuator to move from the second position to the first position when a pre-determined volume of fluid has been dispensed from the second fluid source.

In certain configurations, the actuator is a rotary actuator.

In certain configurations, the rotary actuator causes the valve spool to rotate relative to the valve manifold between the first position and the second position.

In certain configurations, a check valve is associated with the outlet port.

In certain configurations, the actuator is an encoded actuator and the system further includes a sensor configured to detect encoding data from the actuator, and wherein processor is further programmed or configured to determine a position of the actuator based on the encoding data.

In certain configurations, the system further includes a second actuator configured to displace the first fluid source and/or the second fluid source from a first position to a second position.

In certain configurations, the processor is programmed or configured to control, based on data received from the one or more sensors, the second actuator to displace the first fluid source and/or the second fluid source from the first position to the second position.

In certain configurations, the first fluid source and the second fluid source are IV bags, wherein the IV bags are attached to a pole, and wherein the processor is programmed or configured to control, based on data received from the one or more sensors, the second actuator to displace the pole, thereby changing a height of the first fluid source and/or a height of the second fluid source.

In certain configurations, one or more second sensors are associated with the first fluid source and/or the second fluid source, and the one or more second sensors configured to detect an amount of fluid in the first fluid source and/or the second fluid source.

Also provided herein is a computer-implemented method for delivering a plurality of therapeutic compositions to a patient, including providing a first fluid source, a second fluid source, one or more first sensors associated with each of the first fluid source and the second fluid source, and an actuator-actuated valve including a valve manifold having a first inlet port, a second inlet port, and an outlet port, wherein the first inlet port is in fluid communication with the first fluid source and the second inlet port is in fluid communication with the second fluid source, a valve spool extending within the valve manifold, the valve manifold and valve spool defining a first valve passageway and a second valve passageway, wherein the valve spool is moveable relative to the valve manifold between a first position, in which the first inlet port and the outlet port are in fluid communication via the first valve passageway, and a second position, in which the second inlet port and the outlet port are in fluid communication via the second valve passageway, an actuator configured to displace the valve spool relative to the valve manifold between the first position and the second position, delivering, through the first inlet port and from the first fluid source, a first therapeutic composition to a patient, determining, with at least one processor, that a predetermined amount of the first therapeutic has been delivered to the patient, causing, with an actuator controlled by at least one processor, the valve spool to move from the first position to the second position, and delivering, through the second inlet port and from the second fluid source, a second therapeutic composition to the patient.

In certain configurations, the first fluid source and/or the second fluid source are intravenous (IV) drip bags.

In certain configurations, the one or more first sensors include a first flow sensor associated with the first fluid source and a second flow sensor associated with the second fluid source.

In certain configurations, the flow sensors are drip counters.

In certain configurations, the IV drip bags are suspended and the flow sensors are arranged beneath the IV drip bags.

In certain configurations, the system further includes controlling, with at least one processor, the actuator to move from the first position to the second position when a predetermined volume of fluid has been dispensed from the first fluid source.

In certain configurations, the system further includes controlling, with at least one processor, the actuator to move from the second position to the first position when a predetermined volume of fluid has been dispensed from the second fluid source.

In certain configurations, the actuator is a rotary actuator.

In certain configurations, the rotary actuator causes the valve spool to rotate relative to the valve manifold between the first position and the second position.

In certain configurations, the actuator is an encoded actuator.

In certain configurations, the system further includes determining, with at least one processor and a sensor configured to detect encoding data from the actuator, a position of the actuator based on the encoding data.

In certain configurations, a second actuator is configured to displace the first fluid source and/or the second fluid source from a first position to a second position.

In certain configurations, the system further includes controlling, with at least one processor and based at least in part on data received from the one or more sensors, the second actuator to displace the first fluid source and/or the second fluid source from the first position to the second position.

In certain configurations, the first fluid source and the second fluid source are IV bags, and wherein the IV bags are attached to a pole.

In certain configurations, the system further includes controlling, with at least one processor and based at least in part on data received from the one or more sensors, the second actuator to displace the pole, thereby changing a height of the first fluid source and/or a height of the second fluid source.

Also provided herein is a computer-implemented method of delivering therapeutic compositions to a patient, including monitoring, with at least one processor and based at least in part on flow data received from a first sensor, delivery of a first therapeutic composition to a patient, determining, with at least one processor and based at least in part on flow data received from the first sensor, that a predetermined amount of the first therapeutic composition has been delivered to the patient, and in response to determining that a predetermined amount of the first therapeutic composition has been delivered to the patient, causing, with at least one processor, a valve to stop flow of the first therapeutic composition to the patient and to begin flow of a second therapeutic composition to the patient.

DESCRIPTION OF THE INVENTION

Figure 1:
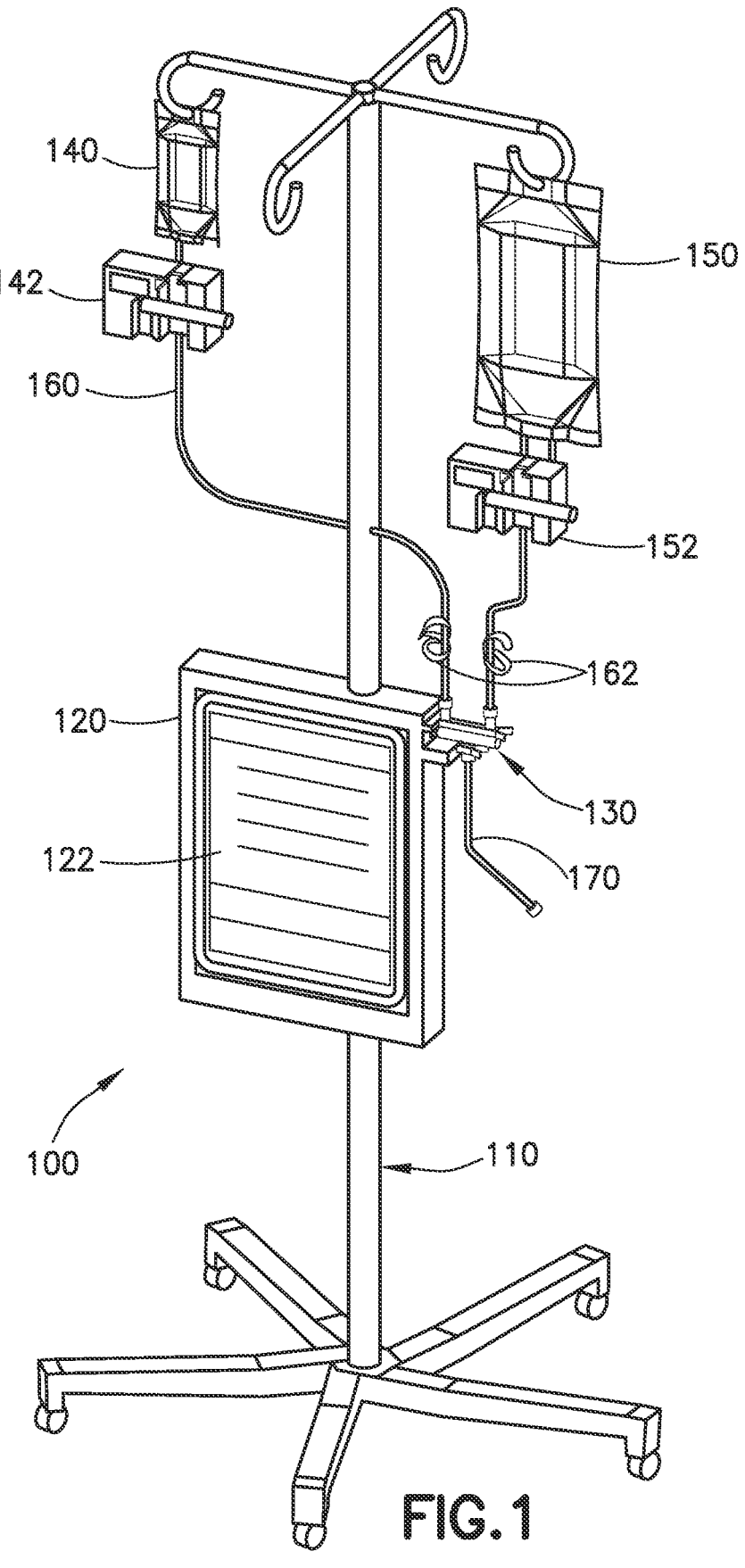
FIG. 1 is a schematic of a system according to non-limiting embodiments described herein.

For purposes of the description hereinafter, the terms "end," "upper," "lower," "right," "left," "vertical," "horizontal," "top," "bottom," "lateral," "longitudinal," and derivatives thereof shall relate to the disclosure as it is oriented in the drawing figures. However, it is to be understood that the disclosure may assume various alternative variations and step sequences, except where expressly specified to the contrary. It is also to be understood that the specific devices and processes illustrated in the attached drawings, and described in the following specification, are simply exemplary embodiments or aspects of the disclosure. Hence, specific dimensions and other physical characteristics related to the embodiments or aspects of the embodiments disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, and/or the like) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or send (e.g., transmit) information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively send information to the second unit. As another example, a first unit may be in communication with a second unit if at least one intermediary unit (e.g., a third unit located between the first unit and the second unit) processes information received from the first unit and sends the processed information to the second unit. In some non-limiting embodiments, a message may refer to a network packet (e.g., a data packet and/or the like) that includes data.

As used herein, the term "computing device" may refer to one or more electronic devices that are configured to directly or indirectly communicate with, or over, one or more networks. In some non-limiting embodiments, a computing device may include a mobile device. A mobile device may include a smartphone, a portable computer, a wearable device (e.g., watches, glasses, lenses, clothing, and/or the like), a personal digital assistant (PDA), and/or other like devices. In some non-limiting embodiments, a computing device may include a server, a desktop computer, and/or the like.

As used herein, the term "system" may refer to one or more computing devices or combinations of computing devices such as, but not limited to, processors, servers, client devices, software applications, and/or other like components. In addition, reference to "a server" or "a processor," as used herein, may refer to a previously-recited server and/or processor that is recited as performing a previous step or function, a different server and/or processor, and/or a combination of servers and/or processors. For example, as used in the specification and the claims, a first server and/or a first processor that is recited as performing a first step or function may refer to the same or different server and/or a processor recited as performing a second step or function.

Provided herein are devices, systems, and methods for delivering a therapeutic, such as a medication, intravenously. The devices, systems, and methods improve accuracy in sequential delivery of therapeutics, through use of a closed-loop system, such that the system ensures patency and flushing, to allow for delivery of highly accurate quantities of medication.

Turning to FIGS. 1 and 3-5, shown is a non-limiting embodiment of a system 100, which may include a pole 110 for mounting the various components of the system 100. These components include flow controller 120, valve 132, sensors 142, 152, and fluid source(s) 140, 150. Flow controller 120 may include a computing device as described herein, which may be programmed or configured to control valve 132 through actuator 134, thereby controlling delivery of fluids (e.g., therapeutic compositions) through valve 132 to a patient. Flow controller 120 may include a display 122. Display 122 may be an interactive graphical user interface (GUI), for example a touch screen, to allow a user to view delivery status of one or more therapeutics from fluid source(s) 140, 150 and, optionally, control actuator 134.

In non-limiting embodiments, fluid source(s) 140, 150 may include one or more associated sensors on or adjacent thereto. In non-limiting embodiments, flow controller 120 and/or actuator 134 receives data from sensors 142, 152 and, based on the received data, determines whether valve 132 should be moved to stop and/or start delivery from fluid source(s) 140, 150. In non-limiting embodiments, actuator 134 and flow controller 120 may be a single device, or actuator 134 may be in wired or wireless communication with flow controller 120, and may include its own processor, memory, and like components of a computing device as described herein.

In non-limiting embodiments, sensors 142, 152 are flow sensors, as are known to those of skill in the art. In non-limiting embodiments, sensors 142, 152 are drip sensors (e.g., sensors configured to count a number of drips from fluid source(s) 140, 150). Sensors 142, 152 may be in wired or wireless communication with flow controller 120 and/or actuator 134. In non-limiting embodiments, one or more additional sensors may be included in system 100, for example, sensors (e.g., optical sensors) may be included to determine an amount of fluid (e.g., therapeutic composition) in fluid source(s) 140, 150. As with all sensors described herein, such sensors may be in communication with flow controller 120 and/or actuator 134.

Fluid source(s) 140, 150 may be any useful type of container known to those of skill in the art. In non-limiting embodiments, fluid source(s) 140, 150 are intravenous (IV) drip bags. Fluid source(s) 140, 150 may contain the same or different therapeutic compositions. In non-limiting embodiments, first fluid source 140 holds a first therapeutic composition, optionally saline, and second fluid source 150 holds a second therapeutic composition, optionally a chemotherapeutic. System 100 may further include tubing 160 to fluidly connect fluid source(s) 140, 150 to valve 132. Tubing 160 may further include one or more line clamps 162, to allow for manual cessation/initiation of fluid delivery. System 100 may also include an intravenous (IV) line 170 between valve 132 and patient, for example IV line 170 may connect valve 132 to an indwelling catheter.

Figure 2A:
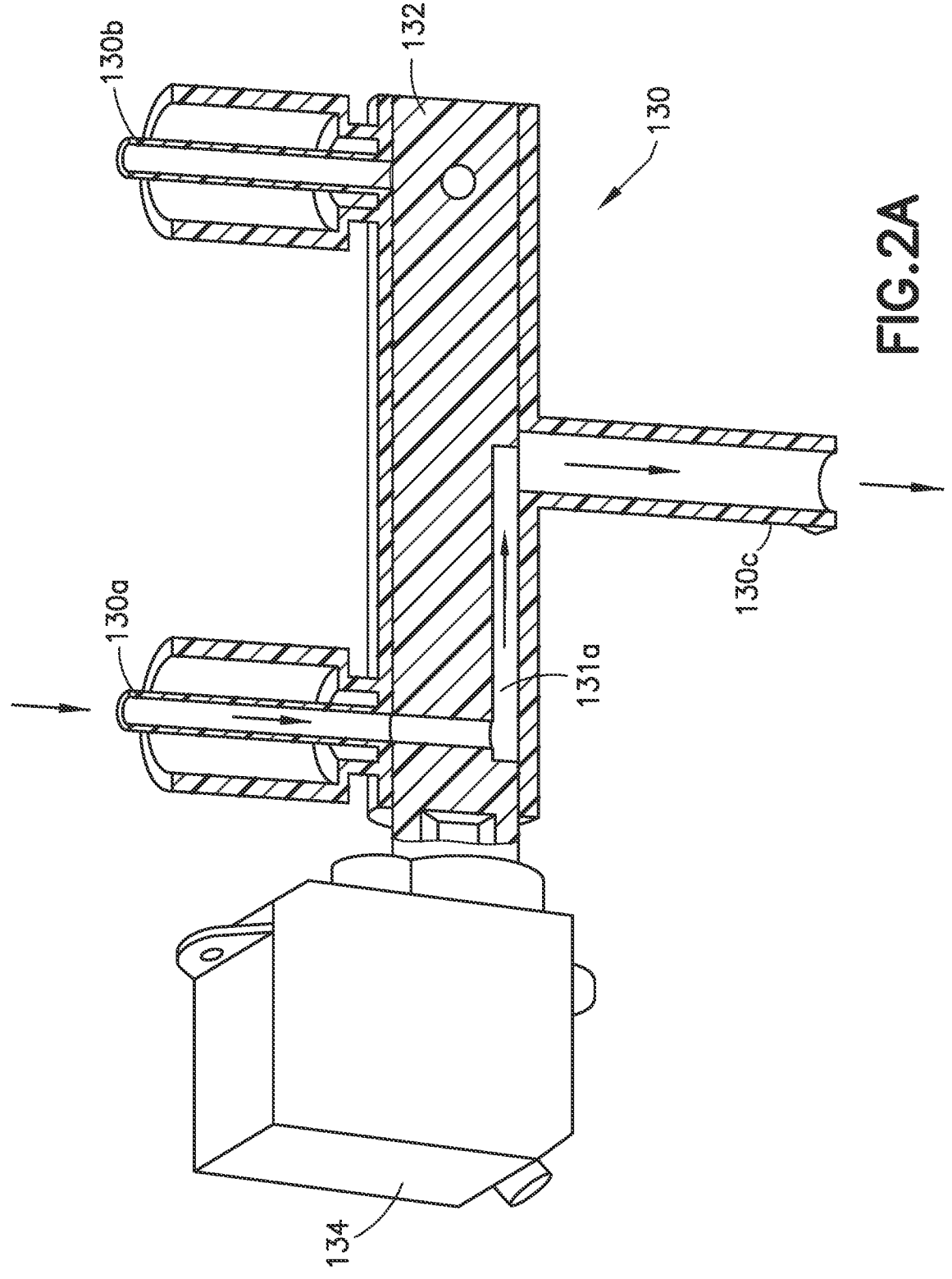
FIGS. 2A-2B are cross-sectional views of a valve useful in systems according to non-limiting embodiments described herein.
Figure 2B:
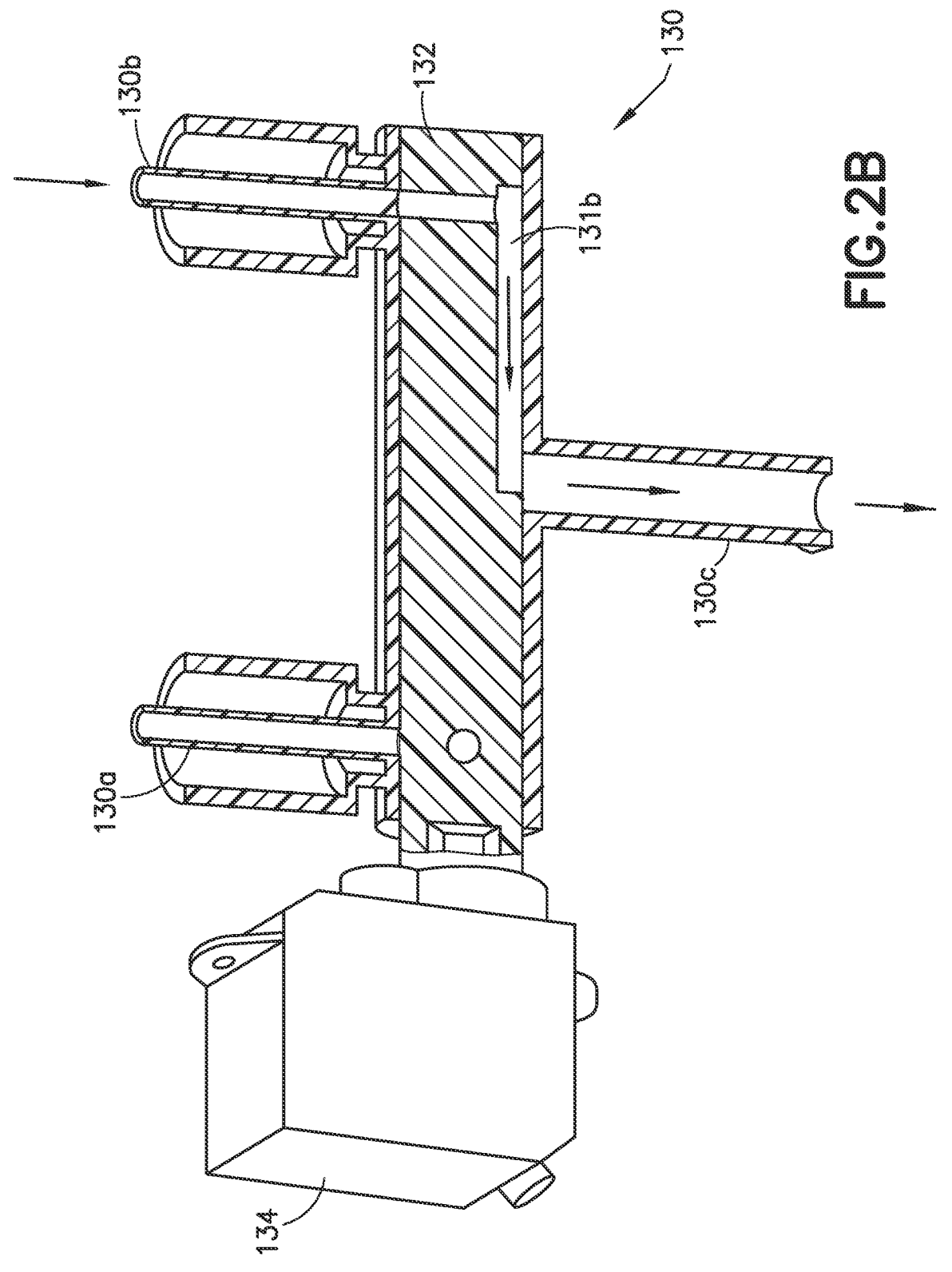
Figure 3:
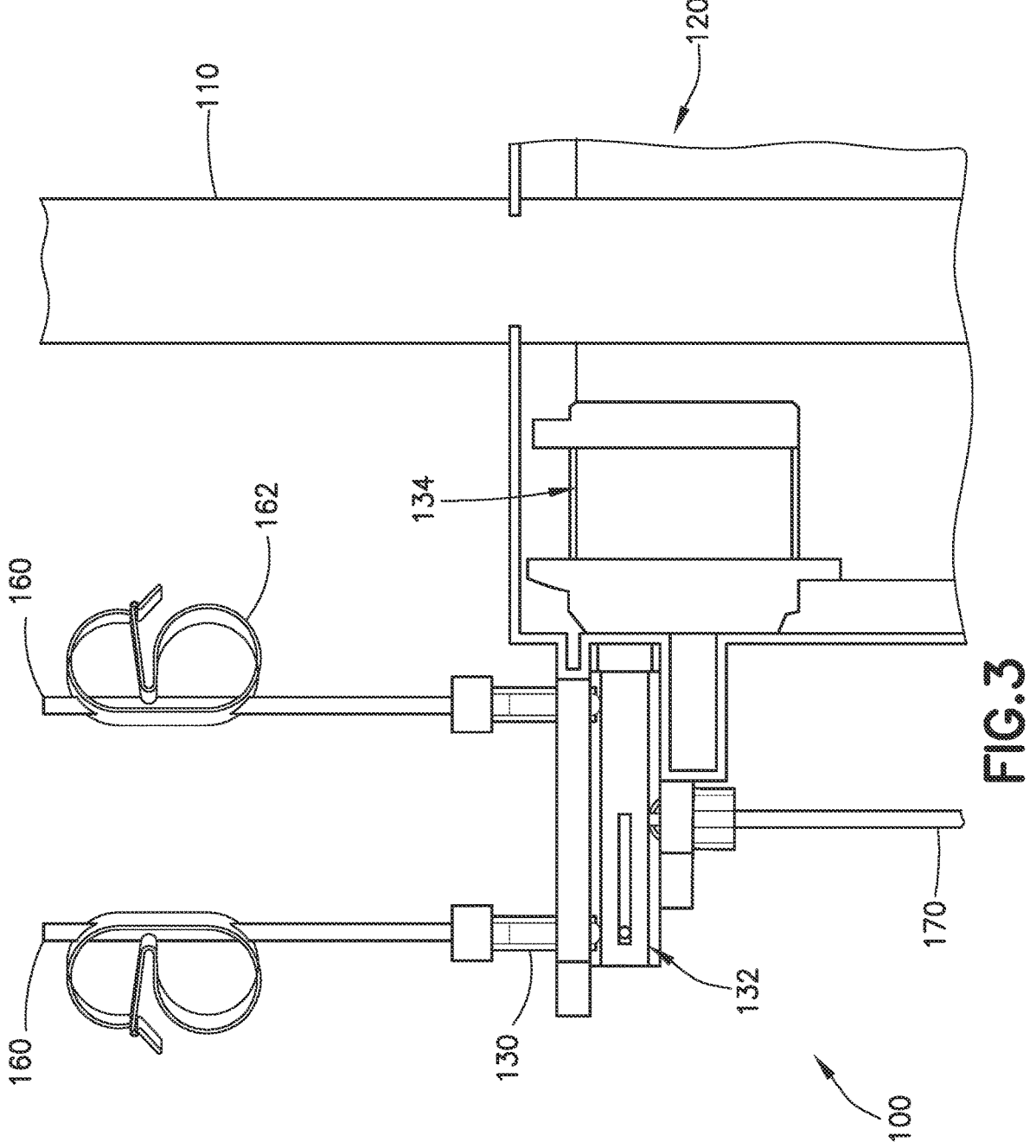
FIG. 3 is a schematic of a system according to non-limiting embodiments described herein.

With regard to the valve 132, FIGS. 2A-2B show cross-sectional views of non-limiting embodiments of a valve 132, including housing (e.g., manifold) 130, inlet ports 130a, 130b, outlet port 130c, and fluid flow paths 131a, 131b within manifold 130. Valve 132 may be a valve as described in U.S. Provisional Patent Application No. 63/338,677, the content of which is incorporated herein by reference in its entirety. Valve 132 may be an actuator-actuated valve, wherein such valve 132 may be acted on by an actuator, such as actuator 134 as described herein, to move between open and closed states.

Figure 4:
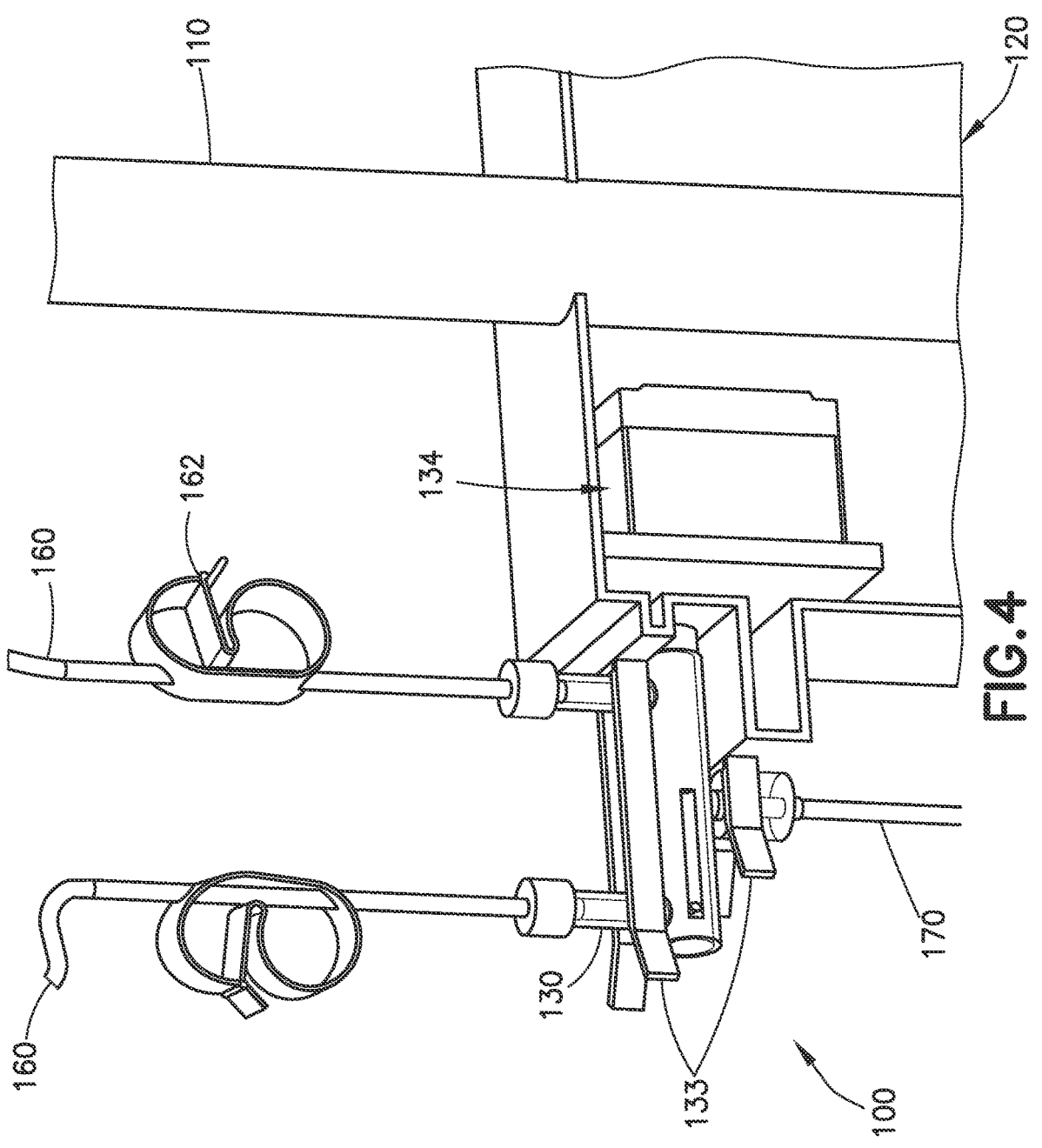
FIG. 4 is a schematic of a system according to non-limiting embodiments described herein.
Figure 5:
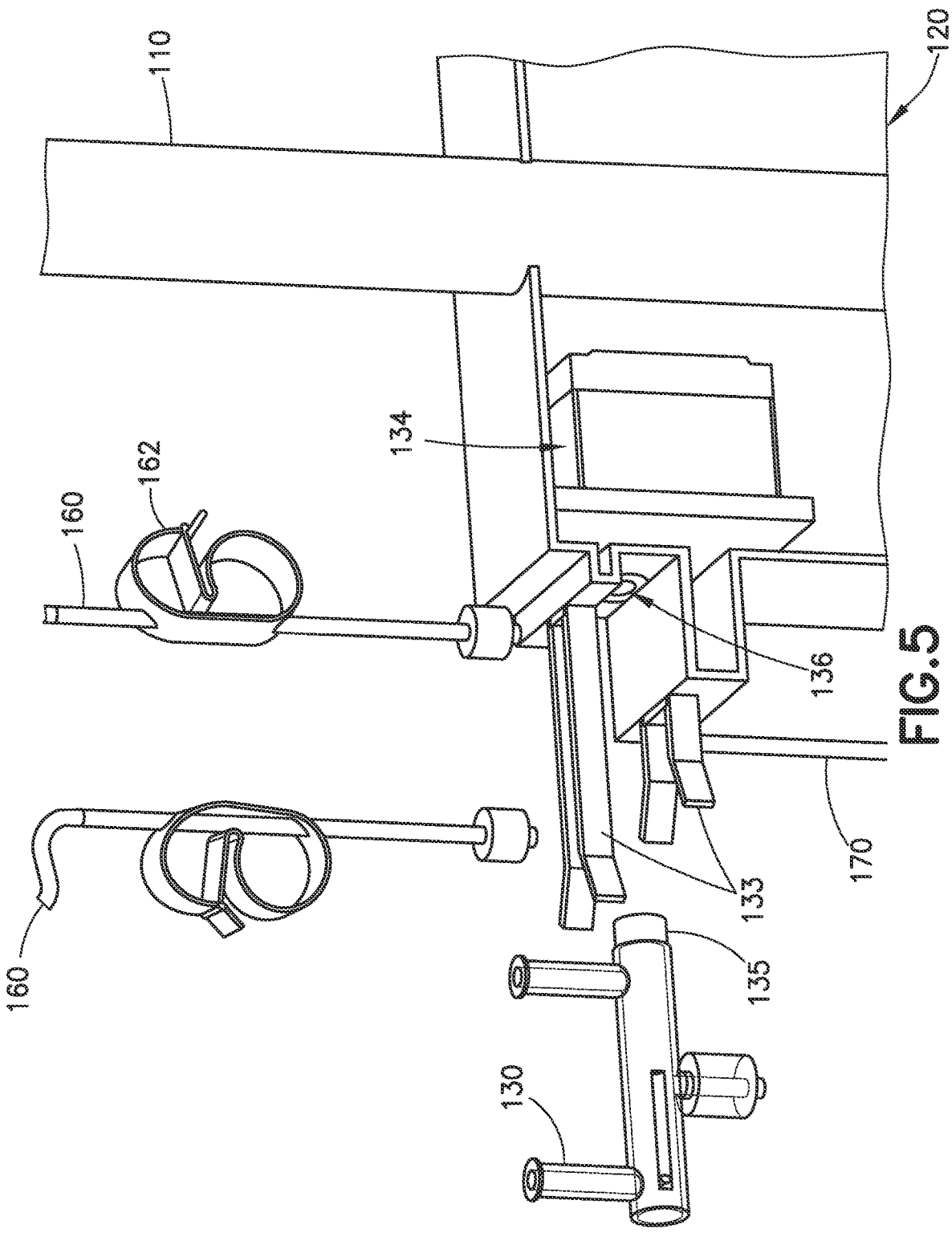
FIG. 5 is a schematic of a system according to non-limiting embodiments described herein.

With continuing reference to the figures, inlet ports 130a, 130b may be in fluid communication with fluid sources 140, 150, respectively. Valve 132 may be a valve spool, optionally a rotatable valve spool, such that as valve 132 is rotated, it is advanced/retracted in manifold 130, from a first position in which first inlet port 130a (FIG. 2A) is in fluid communication with outlet port 130c through fluid flow path 131a (FIG. 2A), to a second position, in which second inlet port 130b is in fluid communication with outlet port 130c through second fluid flow path 131b (FIG. 2B). Outlet port 130c may include a check valve. As shown in FIG. 5, actuator 134 may include a shaft 136 that mates with a corresponding head 135 on valve 132. Shaft 136 may be a male fitting and shaft head 135 may be a female fitting, alternatively shaft 136 may be a female fitting and shaft head 135 may be a male fitting. Valve 132 may be held in place on a housing of fluid controller 120 with a bracket 133, as shown in FIGS. 4 and 5. In non-limiting embodiments, first fluid source 140 is in fluid communication, or may be placed into fluid communication, with first inlet port 130*a*, and second fluid source 150 is in fluid communication, or may be placed into fluid communication, with second inlet port 130*b*.

With continuing reference to the figures, as noted above, valve 132 may be an actuator-actuated valve, and system 100 may further include actuator 134. Actuator 134 may be a rotary actuator, and may cause valve 132 to rotate as valve 132 moves between a first position and a second position as described herein. In non-limiting embodiments, actuator 134 is a servo. As is known in the art, a servo involves use of an encoded actuator, where positioning of the actuator may be read based on the encoding on the device. In non-limiting embodiments, actuator 134 is encoded and a position of actuator 134 is detected by a processor included in actuator 134 and/or flow controller 120, optionally through use of a sensor for reading the encoding on actuator 134.

In non-limiting embodiments, in addition to controlling actuation of valve 132, flow controller 120 may also control a positioning of fluid source(s) 140, 150 through a separate actuator (not shown). In non-limiting embodiments, system 100 includes a linear actuator that may cause a height of fluid source(s) 140, 150 to be changed, either individually or together, based on commands received from flow controller 120.

Figure 6:
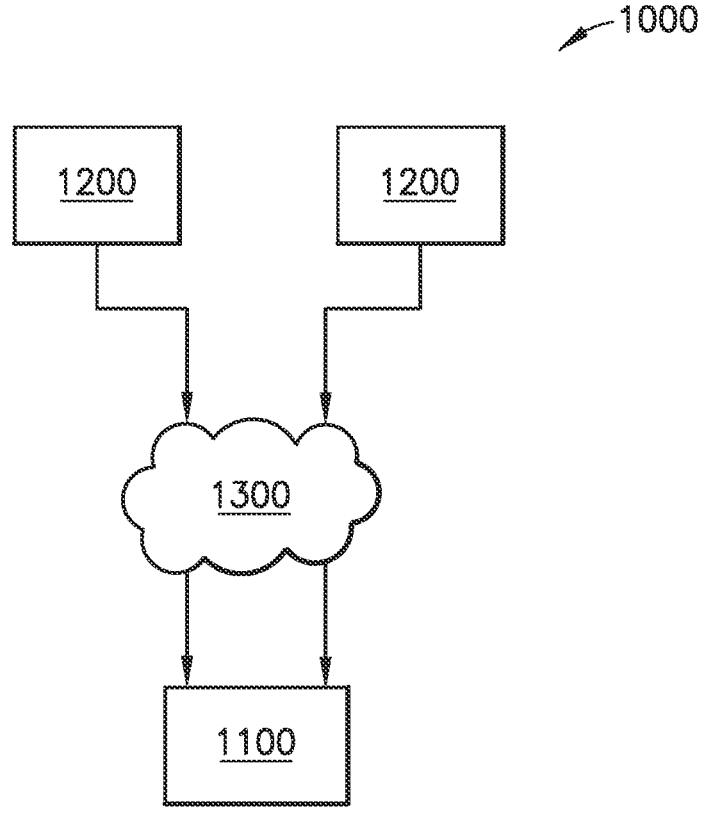
FIG. 6 is a schematic of a system according to non-limiting embodiments described herein.

As described herein, flow controller 120 and/or actuator 134 may include a computing device (as described herein) to initiate and cease delivery of therapeutic compositions, based on data received from one or more sensors included in system 100. Turning now to FIG. 6, in non-limiting embodiments, such a system 1000 includes a communication network 1300, to provide connectivity between various components of the system, for example between sensors 1200 and flow controller 1100 (and/or actuator). Communication network 1300 may include one or more wired and/or wireless networks. For example, communication network 1300 may include a cellular network (e.g., a long-term evolution (LTE) network, a third generation (3G) network, a fourth generation (4G) network, a fifth generation (5G) network, a code division multiple access (CDMA) network, and/or the like), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, and/or the like, and/or a combination of some or all of these or other types of networks.

Figure 7:
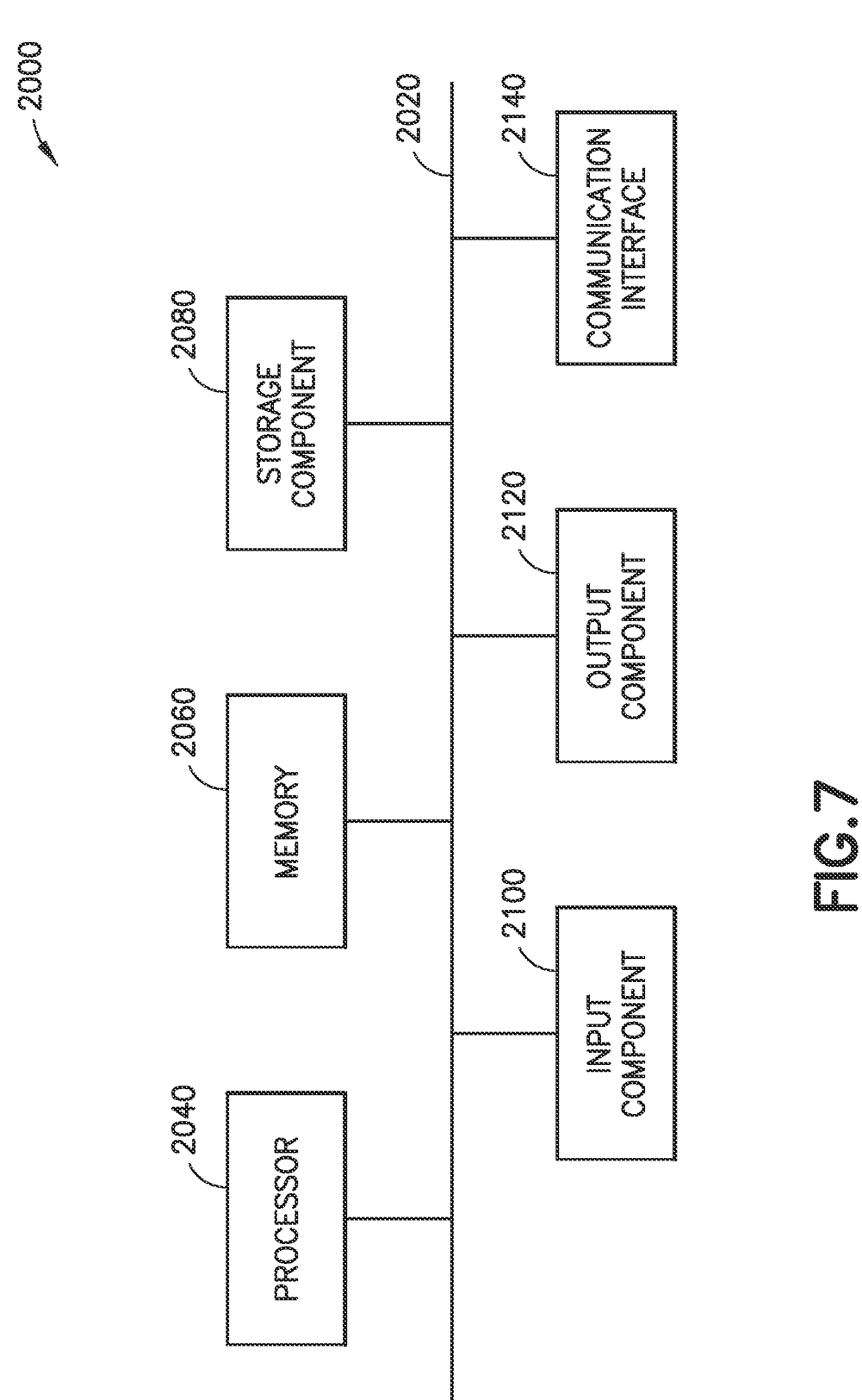
FIG. 7 is a schematic of a computing device useful in systems according to non-limiting embodiments described herein.

Referring now to FIG. 7, illustrated is a diagram of example components of device 2000. Device 2000 may correspond to a flow controller 1100, an actuator, and/or communication network 1300 (e.g., one or more devices of communication network 1300). In some non-limiting embodiments or aspects, flow controller 1100 and/or communication network 1300 may include at least one computer device 2000 and/or at least one component of device 2000. As illustrated in FIG. 7, device 2000 may include bus 2020, processor 2040, memory 2060, storage component 2080, input component 2100, output component 2120, and/or communication interface 2140.

Bus 2020 may include a component that permits communication among the components of device 2000. In some non-limiting embodiments or aspects, processor 2040 may be implemented in hardware, software, or a combination of hardware and software. For example, processor 2040 may include a processor (e.g., a central processing unit (CPU), a graphics processing unit (GPU), an accelerated processing unit (APU), and/or the like), a microprocessor, a digital signal processor (DSP), and/or any processing component (e.g., a field-programmable gate array (FPGA), an application-specific integrated circuit (ASIC), and/or the like) that can be programmed to perform a function. Memory 2060 may include random access memory (RAM), read-only memory (ROM), and/or another type of dynamic or static storage device (e.g., flash memory, magnetic memory, optical memory, and/or the like) that stores information and/or instructions for use by processor 2040.

Storage component 2080 may store information and/or software related to the operation and use of device 2000. For example, storage component 2080 may include a hard disk (e.g., a magnetic disk, an optical disk, a magneto-optic disk, a solid state disk, and/or the like), a compact disc (CD), a digital versatile disc (DVD), a floppy disk, a cartridge, a magnetic tape, and/or another type of computer-readable medium, along with a corresponding drive.

Input component 2100 may include a component that permits device 2000 to receive information, such as via user input (e.g., a touchscreen display, a keyboard, a keypad, a mouse, a button, a switch, a microphone, a camera, and/or the like). Additionally or alternatively, input component 2100 may include a sensor for sensing information (e.g., a global positioning system (GPS) component, an accelerometer, a gyroscope, an actuator, and/or the like). Output component 2120 may include a component that provides output information from device 2000 (e.g., a display, a speaker, one or more light-emitting diodes (LEDs), and/or the like).

Communication interface 2140 may include a transceiver-like component (e.g., a transceiver, a separate receiver and transmitter, and/or the like) that enables device 2000 to communicate with other devices, such as via a wired connection, a wireless connection, or a combination of wired and wireless connections. Communication interface 2140 may permit device 2000 to receive information from another device and/or provide information to another device. For example, communication interface 2140 may include an Ethernet interface, an optical interface, a coaxial interface, an infrared interface, a radio frequency (RF) interface, a universal serial bus (USB) interface, a Wi-Fi© interface, a cellular network interface, and/or the like.

Device 2000 may perform one or more processes described herein. Device 2000 may perform these processes based on processor 2040 executing software instructions stored by a computer-readable medium, such as memory 2060 and/or storage component 2080. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into memory 2060 and/or storage component 2080 from another computer-readable medium or from another device via communication interface 2140. When executed, software instructions stored in memory 2060 and/or storage component 2080 may cause processor 2040 to perform one or more processes described herein. Additionally or alternatively, hardwired circuitry may be used in place of or in combination with software instructions to perform one or more processes described herein. Thus, embodiments or aspects described herein are not limited to any specific combination of hardware circuitry and software.

Memory 2060 and/or storage component 2080 may include data storage or one or more data structures (e.g., a database, and/or the like). Device 2000 may be capable of retrieving information from, storing information in, or searching for information stored in the data storage or one or more data structures in memory 2060 and/or storage component 2080. For example, the information may include encryption data, input data, output data, transaction data, account data, or any combination thereof.

The number and arrangement of components shown in FIG. 7 are provided as an example. In some non-limiting embodiments or aspects, device 2000 may include additional components, fewer components, different components, or differently arranged components than those shown in FIG. 7. Additionally or alternatively, a set of components (e.g., one or more components) of device 2000 may perform one or more functions described as being performed by another set of components of device 2000.

Figure 8:
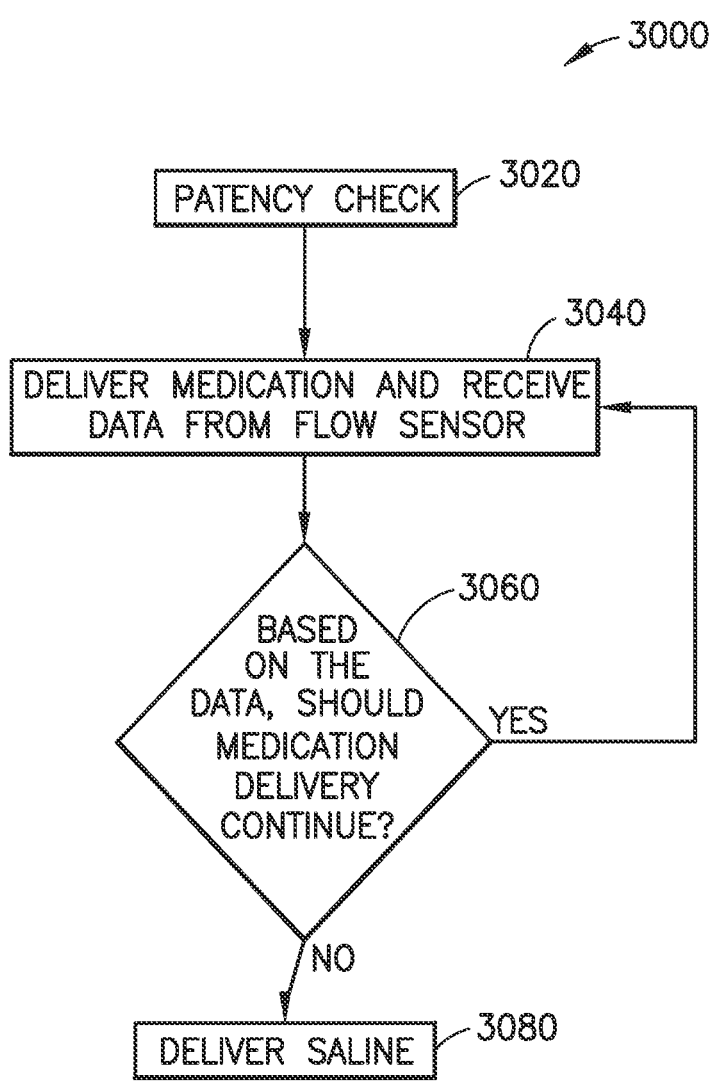
FIG. 8 is a flowchart of a method according to non-limiting embodiments described herein.

With reference to FIG. 8, in non-limiting embodiments, a flow controller and/or actuator as disclosed herein, through one or more processors, may control delivery of a first therapeutic composition. In non-limiting embodiments, the first therapeutic composition is saline, delivered for a check of lumen patency (FIG. 8, 3020). In non-limiting embodiments, about 10 mL of saline is delivered, at a flow rate of about 100 mL/hr. In non-limiting embodiments, flow controller 120 and/or actuator 134 controls valve 132 to deliver a second therapeutic composition, optionally 50 mL at a flow rate of 100 mL/hr, and receives data from one or more sensors associated with a fluid source holding the second therapeutic composition (FIG. 8, 3040). Based at least in part on data received from the sensors, the flow controller 120 determines whether a predetermined amount of the second therapeutic has been delivered to the patient, and whether delivery should continue. If the predetermined threshold or amount has not been met (YES), delivery of the second therapeutic composition continues (FIG. 8, 3040), and the flow controller 120 and/or actuator 134 continues to monitor and determine whether delivery should continue (FIG. 8, 3060). If the predetermined threshold or amount has been met (NO), delivery does not continue, and flow controller 120 and/or actuator 134 controls valve 132 to stop delivery of the second therapeutic composition and, optionally, deliver the first therapeutic composition (FIG. 8, 3080), optionally 50 mL of saline at a flow rate of 100 mL/hr, optionally for flushing components of an intravenous infusion set. In non-limiting embodiments, as described, flow controller 120 may control a further actuator for adjusting relative positioning of fluid sources 140, 150. For example, flow controller 120 may cause a relative change in height between first and second fluid sources 140, 150, to further aid in delivery of a therapeutic composition (e.g., to overcome an obstruction in a fluid line). In non-limiting embodiments, flow controller 120 and/or actuator 134 may use data relating to a height of one or more fluid source(s) 140, 150 to determine pressure within tubing 160, within IV line 170, and, optionally, within the patient's vasculature. In non-limiting embodiments, one or more additional sensors provide data to flow controller 120 and/or actuator 134 to inform determinations concerning initiation of delivery. For example, fluid level sensors associated with fluid sources 140, 150 may transmit data to flow controller 120 and/or actuator 134 to provide an indication of the amount of a therapeutic composition that has been delivered and/or that remains in the fluid source.

Although the above devices, systems, and methods have been described in detail for the purpose of illustration based on what is currently considered to be the most practical and preferred embodiments or aspects, it is to be understood that such detail is solely for that purpose and that the present disclosure is not limited to the described embodiments or aspects but, on the contrary, is intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiments or aspects.

The invention claimed is:

1. A system for sequential delivery of therapeutic compositions according to medication prescription parameters, comprising:

a first fluid source containing a first therapeutic composition and a second fluid source containing second therapeutic composition different than the first therapeutic composition;

one or more first sensors associated with each of the first fluid source and the second fluid source;

one or more second sensors associated with the first fluid source and/or the second fluid source, the one or more second sensors configured to detect an amount of fluid in the first fluid source and/or the second fluid source;

an actuator-actuated valve comprising:

a valve manifold comprising a first inlet port, a second inlet port, and an outlet port, wherein the first inlet port is in fluid communication with the first fluid source and the second inlet port is in fluid communication with the second fluid source;

a valve spool extending within the valve manifold, the valve manifold and valve spool defining a first valve passageway and a second valve passageway, wherein the valve spool is moveable relative to the valve manifold between a first position in which the first inlet port and the outlet port are in fluid communication via the first valve passageway and a second position in which the second inlet port and the outlet port are in fluid communication via the second valve passageway; and an actuator configured to displace the valve spool relative to the valve manifold between the first position and the second position; and a processor in communication with the one or more first sensors and the one or more second sensors, the processor configured to control, based on flow data received from the one or more first sensors that a predetermined amount of the first therapeutic composition has been delivered to the patient, and in response to determining that the predetermined amount of the first therapeutic composition has been delivered to the patient, causing the actuator to displace the valve spool relative to the valve manifold between the first position and the second position to maintain an accurate flow rate and an accurate flow sequence of the first therapeutic composition and the second therapeutic composition according to the medication prescription parameters.

2. The system of claim 1, wherein the first therapeutic composition comprises a medication and the second therapeutic composition comprises saline configured for flushing components of the system.

3. The system of claim 2, wherein the one or more first sensors comprise a first flow sensor associated with the first fluid source and a second flow sensor associated with the second fluid source.

4. The system of claim 3, wherein the first and second flow sensors are drip counters.

5. The system of claim 3, wherein the first fluid source and the second fluid source are IV drip bags that are suspended and the first and second flow sensors are arranged beneath the IV drip bags.

6. The system of claim 3, wherein the processor is further configured to control the actuator to move from the first position to the second position when a pre-determined volume of fluid has been dispensed from the first fluid source.

7. The system of claim 3, wherein the processor is further configured to control the actuator to move from the second position to the first position when a pre-determined volume of fluid has been dispensed from the second fluid source.

8. The system of claim 1, wherein the actuator is a rotary actuator.

9. The system of claim 8, wherein the rotary actuator causes the valve spool to rotate relative to the valve manifold between the first position and the second position.

10. The system of claim 1, further comprising: a check valve associated with the outlet port.

11. The system of claim 1, wherein the actuator is an encoded actuator and the system further includes a data sensor configured to detect encoding data from the actuator, and wherein the processor is further configured to determine a position of the actuator based on the encoding data.

12. The system of claim 1, further comprising: a second actuator configured to displace the first fluid source and/or the second fluid source from a first position to a second position.

13. The system of claim 12, wherein the processor is configured to control, based on data received from the one or more first sensors, the second actuator to displace the first fluid source and/or the second fluid source from the first position to the second position.

14. The system of claim 13, wherein the first fluid source and the second fluid source are IV bags, wherein the IV bags are attached to a pole, and wherein the processor is configured to control, based on data received from the one or more first sensors, the second actuator to displace the pole, thereby changing a height of the first fluid source and/or a height of the second fluid source.

15. The system of claim 1, wherein in the system is a closed loop system configured to ensure patency and flushing of the system.

16. A computer-implemented method for delivering a plurality of therapeutic compositions to a patient through a system according to medication prescription parameters, the method comprising:
 providing:
  a first fluid source;
  a second fluid source;
  one or more first sensors associated with each of the first fluid source and the second fluid source;
  one or more second sensors associated with the first fluid source and/or the second fluid source, the one or more second sensors configured to detect an amount of fluid in the first fluid source and/or the second fluid source;

and
 an actuator-actuated valve comprising:
  a valve manifold comprising a first inlet port, a second inlet port, and an outlet port, wherein the first inlet port is in fluid communication with the first fluid source and the second inlet port is in fluid communication with the second fluid source;
  a valve spool extending within the valve manifold, the valve manifold and valve spool defining a first valve passageway and a second valve passageway, wherein the valve spool is moveable relative to the valve manifold between a first position in which the first inlet port and the outlet port are in fluid communication via the first valve passageway and a second position in which the second inlet port and the outlet port are in fluid communication via the second valve passageway; and
  an actuator configured to displace the valve spool relative to the valve manifold between the first position and the second position;
 delivering, through the first inlet port and from the first fluid source, a first therapeutic composition to a patient;
 determining, with at least one processor, that a predetermined amount of the first therapeutic composition has been delivered to the patient;
 in response to determining that the predetermined amount of the first therapeutic composition has been delivered to the patient, causing, with the actuator controlled by at least one processor, the valve spool to move from the first position to the second position; and
 delivering, through the second inlet port and from the second fluid source, a second therapeutic composition to the patient to maintain an accurate flow rate and an accurate flow sequence of the first therapeutic composition and the second therapeutic composition according to the medication prescription parameters, the second therapeutic composition different than the first therapeutic composition.

17. The method of claim 16, wherein the first therapeutic composition comprises a medication and/or the second therapeutic composition comprises saline configured for flushing components of the system.

18. The method of claim 17, wherein the one or more first sensors comprise a first flow sensor associated with the first fluid source and a second flow sensor associated with the second fluid source.

19. The method of claim 18, wherein the first and second flow sensors are drip counters.

20. The method of claim 18, wherein the first fluid source and the second fluid source are IV drip bags that are suspended, and the first and second flow sensors are arranged beneath the IV drip bags.

21. The method of claim 18, further comprising: controlling, with the at least one processor, the actuator to move the valve spool from the first position to the second position when a pre-determined volume of fluid has been dispensed from the first fluid source.

22. The method of claim 18, further comprising: controlling, with the at least one processor, the actuator to move the valve spool from the second position to the first position when a pre-determined volume of fluid has been dispensed from the second fluid source.

23. The method of claim 16, wherein the actuator is a rotary actuator.

24. The method of claim 23, wherein the rotary actuator causes the valve spool to rotate relative to the valve manifold between the first position and the second position.

25. The method of claim 16, wherein the actuator is an encoded actuator.

26. The method of claim 25, further comprising:

determining, with the at least one processor and a data sensor configured to detect encoding data from the actuator, a position of the actuator based on the encoding data.

27. The method of claim 16, further comprising:

a second actuator configured to displace the first fluid source and/or the second fluid source from a first position to a second position.

28. The method of claim 27, further comprising:

controlling, with at least one processor and based at least in part on data received from the one or more first sensors, the second actuator to displace the first fluid source and/or the second fluid source from the first position to the second position.

29. The method of claim 28, wherein the first fluid source and the second fluid source are IV bags, and wherein the IV bags are attached to a pole.

30. The method of claim 29, further comprising:

controlling, with the at least one processor and based at least in part on data received from the one or more first sensors, the second actuator to displace the pole, thereby changing a height of the first fluid source and/or a height of the second fluid source.

31. A computer-implemented method of delivering therapeutic compositions to a patient according to medication prescription parameters, the method comprising:

monitoring, with at least one processor and based at least in part on flow data received from a first sensor, delivery of a first therapeutic composition to a patient;

determining, with the at least one processor and based at least in part on flow data received from the first sensor, that a predetermined amount of the first therapeutic composition has been delivered to the patient; and in response to determining that the predetermined amount of the first therapeutic composition has been delivered to the patient, causing, with the at least one processor, a valve to stop flow of the first therapeutic composition to the patient and begin flow of a second therapeutic composition to the patient and to maintain an accurate flow rate and an accurate flow sequence of the first therapeutic composition and the second therapeutic composition according to the medication prescription parameters, the second therapeutic composition different than the first therapeutic composition.

* * * * *